United States Patent [19]

McFadden

[11] Patent Number: 5,574,010
[45] Date of Patent: Nov. 12, 1996

[54] TREATMENT OF PANCREATIC TUMORS WITH PEPTIDE YY AND ANALOGS THEREOF

[75] Inventor: David W. McFadden, Los Angeles, Calif.

[73] Assignee: The Regents of The University of California, Oakland, Calif.

[21] Appl. No.: 338,395

[22] Filed: Nov. 14, 1994

[51] Int. Cl.$^6$ .............................. A61K 38/00; C07K 5/00; C07K 7/00
[52] U.S. Cl. .............................. 514/12; 530/324; 530/300
[58] Field of Search .................... 514/12, 13, 14; 530/327, 326, 325, 324, 300

[56] References Cited

PUBLICATIONS

Pappas et al., Gastroenterology (1985) 89 pp. 1387–1392.
Blackmore et al., Br. J. Cancer, (1992) 66 32–38.
Palmer Smith et al., Am. J. Physiol. (1993) 265 (1, pt. 1) pp. G149–G155.
Harper's Review of Biochemistry, pp. 559–561 (Copyright 1985—Lange Medical Publications).
Laburthe, M., "Peptide YY and Neuropeptide Y in the Gut/Availability, Biological Actions, and Receptors," *Trends in Endocrinology and Metabolism*, In press, Dec. 1989, pp. 035–041.
Rämö et al., "Neuropeptide Y and Peptide YY Stimulate the Growth of Exocrine Pancreatic Carcinoma Cells," *Neuropeptides* (1990) 15, 101–106.
Playford et al., "Preliminary report: role of peptide YY in defence aainst diarrhoea," *The Lancet* (1990) 335, 1555–1557.
Evers et al., "Differential Effects of Gut Hormones on Pancreatic and Intestinal Growth During Administration of an Elemental Diet," *Ann. Surg.* (1990) 211, 5, 630–638.
Sheikh et al., "Localization of $Y_1$ receptors for NPY and PYY on vascular smooth muscle cells in rat pancreas," *Am. Phys. Soc.* (1991) G250–G257.
Leiter et al., "Peptide YY/Structure of the Precursor and Expression in Exocrine Pancreas," *J. Biol. Chem.* (1987) vol. 262, No. 27, pp. 12984–12988.
Balasubramaniam et al., "Structure–Activity Studies of Peptide YY(22–36): N–α–Ac–[Phe$^{27}$]PYY(22–36), a Potent Antisecretory Peptide in Rat Jejunum," *Peptides* (1993) 14, pp. 1011–1016.

*Primary Examiner*—Avis M. Davenport
*Attorney, Agent, or Firm*—Poms, Smith, Lande & Rose

[57] ABSTRACT

A method of inhibiting proliferation of pancreatic tumors. The method involves contacting the pancreatic tumor with an effective amount of peptide YY or an analog of peptide YY.

The method may be used either in vitro or in vivo to reduce tumor cell proliferation. The method is also effective in treating both benign and malignant tumors.

18 Claims, No Drawings

TREATMENT OF PANCREATIC TUMORS WITH PEPTIDE YY AND ANALOGS THEREOF

BACKGROUND OF THE INVENTION

1. Field of the Invention

The present invention relates generally to methods for treating pancreatic tumors. More particularly, the present invention is directed to methods for treating both benign and malignant pancreatic tumors with peptide YY and analogs thereof.

2. Description of Related Art

Pancreatic tumors result in the death of more than 95 percent of afflicted patients. Isselbacher, et al. (ed.) Harrison's Principles of Internal Medicine, 1532–34 (13th ed., 1994). In 1993, approximately 25,000 patients died of pancreatic cancer, making it the fifth most common cause of cancer-related mortality. Cancer Facts and Figures, American Cancer Society (1993).

Pancreatic tumors occur twice as frequently in the pancreatic head (60 percent of cases) as in the body (15–20 percent) or tail (about 5 percent) of the gland. Cotran, et at. (ed.) *Rubbins Pathologic Basis of Disease*, 988–992 (4th ed. 1989). Currently, complete surgical resection of pancreatic tumors offers the only effective treatment of this disease. Surgical resection, however, is limited, for all practical purposes, to those individuals having tumors in the pancreatic head and in whom jaundice was the initial symptom. Even with the operation, the five year survival rate for these patients is only five percent. Isselbacher, et al. (ed.) *Harrison's Principles of Internal Medicine*, 1532–34 (13th ed., 1994).

SUMMARY OF THE INVENTION

The present invention involves a method for treating pancreatic tumor cells to reduce the proliferation of such cells. The method is applicable to both benign and malignant tumors. In addition, the method is useful in both in vivo and in vitro environments.

In accordance with the present invention, it was discovered that peptide YY is an effective anti-proliferation agent which, when contacted with pancreatic tumor cells, is useful in reducing the degree to which the tumor cells proliferate.

As a further feature of the present invention, it was discovered that certain analogs of peptide YY are also effective anti-pancreatic tumor agents.

The method includes the step of contacting the proliferating pancreatic tumor with an effective amount of peptide YY or an analog of peptide YY which are also referred to herein as peptide YY agonists. The contacting step can be carded out according to any of the known procedures for administering drugs to pancreatic tumors including parenteral delivery, e.g. administered to the tumor in a subject intravenously, subcutaneously, by implantation of a sustained release formulation (e.g. near the pancreas), transdermally (e.g. topically or by iontophoretic path), by implantable or external infusion pump, or by perfusion (e.g. of the pancreas). In other embodiments, the contacting step may also be effected externally or transmucously.

The types of benign pancreatic tumor cells which may be treated in accordance with the present invention include serous cyst adenomas, microcystic tumors, and solid-cystic tumors. The method is also effective in reducing the proliferation of malignant pancreatic tumor cells such as carcinomas arising from the ducts, acini, or islets of the pancreas.

Both definition and exemplification of peptide YY, and analogs of peptide YY, i.e. "peptide YY agonist" are set forth in the DESCRIPTION OF THE PREFERRED EMBODIMENTS below.

It was discovered that dosage levels on the order of a few pmol/kg/hour were effective in reducing cell proliferation. Higher dosages ranging up to 1000 pmol/kg/hour and even higher may be used provided that side effects are not too adverse. The most common adverse side effect of administration of peptide YY and its analogs is vomiting. In general the amount of peptide YY or peptide YY analog required to achieve desired therapeutic effectiveness will depend upon the condition being treated, the route of administration chosen, and the specific activity of the compound used, and ultimately will be decided by the attending physician or veterinarian by routine dosage adjustments.

Other features and advantages of the invention will be apparent from the following description of the preferred embodiments thereof, and from the claims.

Abbreviations:

Aib=aminoisobutyric acid

Anb=α-aminonormalbutyric acid

Bip=4,4'-biphenylalanine

Bth=3-benzothienylalanine

Dip=2,2-diphenylalanine

Nat=2-napthylalanine

Orn=Ornithine

Pcp=4-chlorophenylalanine

Thi=2-thienylalanine

Tic=tetrahydroisoquinoline-3-carboxylic acid

DESCRIPTION OF THE PREFERRED EMBODIMENTS

Peptide YY and Its Agonists:

Peptide YY (PYY) is a 36 amino acid residue peptide amide isolated originally from porcine intestine and localized in the endocrine cells of the gastrointestinal tract and the pancreas (Tatemotu et al., 79 *Proc. Natl. Acad. Sci.* 2514 (1982)). The amino acid sequences of porcine and human PYY are as follows:

porcine PYY—YPAKPEAPGEDASPEELSRYYASLRHYLNLVTRQRY (SEQ. ID. NO. 1)

human PYY—YPIKPEAPGEDASPEELNRYYASLRHYLNLVTRQRY (SEQ. ID. NO. 2)

The amino acid sequence for dog PYY and rat is the same as porcine PYY.

PYY is believed to inhibit gut motility and blood flow (Laburthe, 1 *Trends Endocrinol. Metab.* 168 (1990)), to mediate intestinal secretion (Cox et at., 101 Br. *J. Pharmacol.* 247 (1990)); Playford et at., 335 *Cancer* 1555 (1990)), and stimulate net absorption (MacFayden et at., 7 *Neuropeptides* 219 (1986)).

Novel analogs have been prepared in order to emulate and preferably enhance the duration of effect, biological activity, and selectivity of the natural peptide. Many of these analogs are derived from biologically active peptide fragments of PYY (e.g., $PYY_{22-36}$ and $PYY_{25-36}$). Such analogs, which inhibit the proliferation of pancreatic tumors, will be called peptide YY agonists herein.

Peptide YY agonists which can be used to practice the therapeutic method of the present invention include, but are not limited to, those covered by the formulae or those specifically recited in the publications set forth below, all of which are hereby incorporated by reference.

Balasubramaniam, et al., 1 *Peptide Research* 32 (1988);
Japanese Patent Application 2,225,497 (1990);
Balasubramaniam, et al., 14 *Peptides* 1011 (1993);
Grandt, et at., 51 Reg. *Peptides* 151 (1994); and
PCT U.S. application Ser. No. 94/03380 (1994).

Peptide YY agonists which can be used to practice the therapeutic method of the present invention also include the closely related peptide neuropeptide Y (NPY) as well as derivatives, fragments, and analogs of NPY. The amino acid sequences of porcine and human NPY are as follows:

human NPY—YPSKPDNPGEDAPAEDMARYYSAL-RHYINLITRQRY (SEQ. ID. NO. 3)

porcine NPY—NPY YPSKPDNPGEDAPAED-LARYYSALRHYINLITRQRY (SEQ. NO. 4)

The amino acid sequence for rat NPY, rabbit NPY, and guinea pig NPY are the same as human NPY.

Examples of NPY analogs include but are not limited to, those covered by the formulae or those specifically recited in the publications set forth below, all of which are hereby incorporated by reference.

German Patent Application DE 3811193A1 (1989);
Balasubramaniam et al., 265 *J. Biological Chem.*, 14724–14727 (1990);
Cox et al., 101 Br. *J. Pharmacol.*, 247–252 (1990);
PCT Application WO 91/08223 (1991);
U.S. Pat. No. 5,026,685 (1991);
Balasubramaniam et al., 267 *J. Biological Chem.*, 4680–4685 (1992);
European Patent Application 0355793 A3 (1992);
Dumont et al., 238 *European J. Pharmacol.*, 37–45 (1993);
Kirby et al., 36 *J. Med. Chem.*, 3802–3808 (1993);
PCT Application WO 94/00486 (1994);
Fournier et al., 45 *Molecular Pharmacol.*, 93–101 (1994).
Balasubramaniam et al., 37 *J. Med. Chem.*, 811–815 (1994);
Polter et al., 267 *European J. Pharmacol.*, 253–262 (1994); and
U.S. Pat. No. 5,328,899 (1994).

Preferred peptide YY agonists of the invention is of the formula:

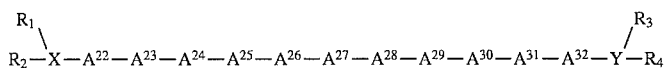

wherein:

X is a chain of 0–5 amino acids, inclusive, the N-terminal one of which is bonded to $R_1$ and $R_2$ Y is a chain of 0–4 amino acids, inclusive, the C-terminal one of which is bonded to $R_3$ and $R_4$ $R_1$ is H, $C_1$–$C_2$ alkyl (e.g., methyl), $C_6$–$C_{18}$ aryl (e.g., phenyl, napthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$R_2$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$A^{22}$ is an aromatic amino acid, Ala, Aib, Anb, N-Me-Ala, or is deleted;

$A^{23}$ is Ser, Thr, Ala, N-Me-Ser, N-Me-Thr, N-Me-Ala, or is deleted;

$A^{24}$ is Leu, Ile, Vat, Trp, Gly, Aib, Anb, N-Me-Leu, or is deleted;

$A^{25}$ is Arg, Lys, homo-Arg, diethyl-homo-Arg, Lys-ε-NH-R (where R is H, a branched or straight chain $C_1$–$C_{10}$ alkyl group, or an aryl group), Orn, or is deleted;

$A^{26}$ is His, Thr, 3-Me-His, 1-Me-His, β-pyrozolylalanine, N-Me-His, Arg, Lys, homo-Arg, diethyl-homo-Arg, Lys-ε-NH-R (where R is H, a branched or straight chain $C_1$–$C_{10}$ alkyl group, or an aryl group), Orn, or is deleted;

$A^{27}$ is an aromatic amino acid other than Tyr;

$A^{28}$ is Leu, Ile, Vat, Trp, Aib, Aib, Anb, or N-Me-Leu;

$A^{29}$ is Asn, Ala, Gln, Gly, Trp, or N-Me-Asn;

$A^{30}$ is Leu, Ile, Val, Trp, Aib, Anb, or N-Me-Leu;

$A^{31}$ is Vat, Ile, Trp, Aib, Anb, or N-Me-Val;

$A^{32}$ is Thr, Ser, N-Me-Set, or N-Me-Thr;

$R_3$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$R_4$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl), or a pharmaceutically acceptable salt thereof.

Particularly preferred agonists of this formula to be used in the method of the invention include:

N-α-Ala-Ser-Leu-Arg-His-Trp-Leu-Asn-Leu-Val-Thr-Arg-Gln-Arg-Tyr-NH$_2$(Analog #1) (SEQ. ID. NO. 5).

Also preferred peptide YY agonists of the invention is of the formula:

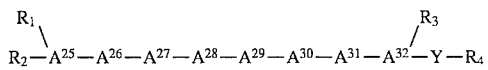

wherein:

the N-terminal amino acid bonds to $R_1$ and $R_2$;

Y is a chain of 0–4 amino acids, inclusive the C-terminal one of which bonds to $R_3$ and $R_4$;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{25}$ is Arg, Lys, homo-Arg, diethyl-homo-Arg, Lys-ε-NH-R (where R is H, a branched or straight chain $C_1$–$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH-R (where R is H, a branched or straight chain $C_1$–$C_{10}$ alkyl group, or an aryl group), Orn or is deleted;

$A^{27}$ is an aromatic amino acid;

$A^{28}$ is Leu, Ile, Val, Trp, Aib, Anb, or N-Me-Leu;

$A^{29}$ is Asn, Ala, Gln, Gly, Trp, or N-Me-Asn;

$A^{30}$ is Leu, Ile, Val, Trp, Aib, Anb, or N-Me-Leu;

$A^{31}$ is Val, Ile, Trp, Aib, Anb, or N-Me-Val;

$A^{32}$ is Thr, Set, N-Me-Set, or N-Me-Thr or D-Trp;

$R_3$ is H, $C_{1-C12}$ alkyl, $C_6$–$C_{18}$ aryl, $C_1$–$C_{12}$ acyl, $C_7$–$C_{18}$ aralkyl, or $C_7$–$C_{18}$ alkaryl; and $R_4$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl, or a pharmaceutically acceptable salt thereof. Note that, unless indicated otherwise, for all peptide YY agonists described herein, each amino acid residue, e.g., Leu and $A^1$, represents the structure of NH—C(R)H—CO—, in which R is the side chain. Lines between amino acid residues represent peptide bonds which join the amino acids. Also, where the amino acid residue is optically active, it is the L-form configuration that is intended unless D-form is expressly designated.

Synthesis of PYY Agonists:

Human PYY, homologues, fragments, and analogs thereof, can be purchased commercially (Bachem California 1993–94 Catalogue, Torrance, Calif.; Sigma Peptides and Amino Acids 1994 Catalog, St. Louis, Miss.). The PYY analogs of the present invention may also be synthesized by many techniques that are known to those skilled in the peptide art. An excellent summary of the many techniques so available may be found in Solid Phase Peptide Synthesis 2nd ed. (Stewart, J. M. and Young, J. D., Pierce Chemical Company, Rockford, Ill. 1984).

Analog #1 (Sequence ID No. 5), obtained from the University of Cincinnati, Cincinnati, Ohio, was synthesized as follows. Peptide synthesis was performed on an Applied Biosystems® (Forster City, Calif.) Model 430A synthesizer. Amino acid and sequence analyses were carried out using Waters® (Milford, Mass.) Pico-Tag and Applied Biosystems® Model 470A instruments, respectively. The peptide was purified using a Waters Model 600 solvent delivery system equipped with a Model 481 Spectrophotometer and U6K injector according to standard protocols. Peptide mass spectra were determined at the University of Michigan, Protein Chemistry Facility, An Arbor, Michigan according to standard methods. All Boc-L-amino acid derivatives, solvents, chemicals and the resins were obtained commercially and used without further purification.

Paramethylbenzhydrylamine (MBHA) resin (0.45 mmol/gm, -$NH_2$) was placed in the reaction vessel of the peptide synthesizer and the protected amino acid derivatives were sequentially coupled using the program provided by the manufacturers modified to incorporate a double coupling procedure (see, e.g., Balasubramaniam et at., *Peptide Research* 1: 32, 1988). All amino acids were coupled using 2.2 equivalents of preformed symmetrical anhydrides. Arg, Gln and Asn, however, were coupled as preformed 1-hydroxybenzotriazole (HOBT) esters to avoid side reactions. At the end of the synthesis, the N-α-Boc group was removed and in some instances the free α-NH2 was acetylated by reaction with acetic anhydride (2 equivalents) and diisopropyl ethylamine until a negative ninhydrin test was obtained (*Anal. Biochem.* 34:595, 1970). The peptide resin (~1.0 g) was then treated with HF (10 ml) containing p-cresol (~0.8 g) for 1 h at −2 to −4° C. The HF was evaporated and the residue was transferred to a fritted filter funnel with diethyl ether, washed repeatedly with diethyl ether, extracted with acetic acid (2×15 ml) and lyophilized. The crude peptides thus obtained were purified by semipreparative RP-HPLC.

Other PYY analogs of the invention can be prepared by making appropriate modifications, within the ability of a person of ordinary skill in this field, of the synthetic methods disclosed herein.

While it is possible for peptide YY and peptide YY analogs to be administered as the pure or substantially pure compounds, it is preferable that they be administered as pharmaceutical formulations or preparation. The formulations to be used in the present invention, for both humans and animals, include peptide PYY any of the analogs set forth above, together with one or more pharmaceutically acceptable carriers therefor, and optionally other therapeutic ingredients.

The carrier must be "acceptable" in the sense of being compatible with the active ingredient(s) of the formulation (and preferably, capable of stabilizing peptides) and not deleterious to the subject to be treated.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for intravenous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampules or vials.

Formulations suitable for sustained release formulations include biodegradable polymers (e.g. U.S. Pat. Nos. 4,678, 189 and 4,767,628, hereinafter incorporated by reference). Examples of suitable biodegradable polymers include L-lactic acid, D-lactic acid, DL-lactic acid, glycolide, glycolic acid, and any optically active isomers, racements, or copolymers thereof.

Peptide YY and peptide YY agonists are administered to pancreatic tumors using the same procedures which are well-known for use in introducing chemotherapeutic agents to pancreatic tumors. The particular route of administration will vary depending upon tumor type, location, extent of growth and other factors. By routine experimentation, the preferred route of administration and dosage regimen can be established on an individual basis. As mentioned previously, the administration routes include: intravenous introduction to the tumor; subcutaneous introduction by implantation of a sustained release device near the tumor; transdermal introduction by topical or ion phoretic application; direct introduction to the tumor by an implantable or external infusion pump; or by perfusion. All of the above administration routes are well-known to those of ordinary skill in the art and have been used in pancreatic tumor treatment protocols using other chemotherapeutic agents.

In order to achieve maximum dosage levels with minimum side-effects, it is preferred that administration techniques be used which introduce peptide YY or peptide YY agonists directly to the tumor. Direct infusion and perfusion are examples. The dosage level may be varied widely depending upon the patients tolerance to the particular peptide YY or analog being administered. Initial trial infusion or perfusion dosages on the order of two to four hundred pmol/kg/hour are preferably used. The dosage level is adjusted upward or downward depending upon patient tolerance and tumor response. Preferably the dosage level is increased to a level which provides a significant (i.e. at least 15 %) reduction in cell proliferation without causing adverse side effects, such as vomiting, abdominal pain or constipation.

The method of the present invention is preferably carried out continuously over extended periods of time to achieve maximum effectiveness. Sustained release devices located adjacent to the tumor are well-suited for providing continual application. Infusion and perfusion is preferably carded out continually for 6 hours up to 168 hours. Patient and tumor response to the treatment is continually monitored during the treatment period with adjustments in dosage levels being made, if necessary. Treatment is terminated when desired levels of reduction in minor cell proliferation are achieved or the patient experiences adverse side effects. It is preferred that treatment times, like dosages, be maximized to achieve maximum reduction in cell proliferation without creating adverse side effects.

Examples of practice are as follows:

EXAMPLE 1

Demonstration of Anti-Proliferative Activity In Vitro

In this example, the effectiveness of PYY and Analog #1 in reducing proliferation of two different pancreatic ductal adenocarcinomas in vitro is demonstrated. PANC-1 and MiaPaCa-2 are two human pancreatic adenocarcinomas cancer cell lines which are available commercially from suppliers such as American Type Culture Collection, ATCC (Rockville, Md.). For this example, the two tumor cells were grown in RPMI-1640 culture media supplemented with 10% fetal bovine serum, 29.2 mg/L of glutamine, 25 µg gentamicin, 5 ml penicillin, streptomycin, and fungizone solution (JRH Biosciences, Lenexa, Kans.) at 37° Celcius in a NAPCO water jacketed 5 % $CO_2$ incubator. All cell lines were detached with 0.25 % trypsin (Clonetics, San Diego, Calif.) once to twice a week when a confluent monolayer of tumor cells was achieved. Cells were pelleted for 7 minutes at 500 g in a refrigerated centrifuge at 4 ° Celcius, and resuspended in trypsin free fortified RPMI 1640 culture media. Viable cells were counted on a hemocytometer slide with trypan blue.

Ten thousand, 20,000, 40,000 and 80,000 cells of each type were added to 96 well microculture plates (Costar, Cambridge, Mass.) in a total volume of 200 µl of culture media per well. Cells were allowed to adhere for 24 hours prior to addition of the PYY or Analog #1 peptides. Fresh culture media was exchanged prior to addition of peptides. In vitro incubation of pancreatic tumor cells with either PYY or Analog #1 was continued for 6 hours and 36 hours in length. PYY was added to cells at doses of 250 pmol, 25 pmol, and 2.5 pmol per well (N =14). Analog #1 was added to cells cultures at doses of 400 pmol, 40 pmol, and 4 pmol per well. Control wells received 2 µl of 0.9% saline to mimic the volume and physical disturbance upon adhered tumor cells. Each 96 well plate contained 18 control wells to allow for comparison within each plate during experimentation. Ninety-six (96) well plates were repeated 6 times with varying concentrations of PYY and Analog #1 in both the PANC-1 and MiaPaCa-2 cells.

At the end of the incubation period, 3-(4,5-dimethylthiazolyl-2-yl)-2,5-diphenyltetrazolium Bromide, MTr tetrazolium bromide (Sigma, St. Louis, Mo.) was added to fresh culture media at 0.5 mg/ml. Culture media was exchanged and tumor cells were incubated for 4 hours with MTT tetrazolium bromide at 37° Celcius. At the end of incubation, culture media was aspirated. Formazon crystal precipitates were dissolved in 200 µl of dimethyl sulfoxide (Sigma, St. Louis, Mo.). Quantitation of solubilized formazon was performed by obtaining absorption readings at 500 nm wavelength on an ELISA reader (Molecular Devices, Menlo Park, Calif.). The MTT assay measures mitochondrial NADH dependent dehydrogenase activity, and it has been among the most sensitive and reliable method to quantitative in vitro chemotherapy responses of tumor cells. (Alley, M. C., Scudiero, D. A., Monk, A., Hursey, M. L., Dzerwinski, M. J., Fine, D. L., Abbott, B. J., Mayo, J. G., Shoemaker, R. H. and Boyd, M. R., Feasibility of drug screening with panels of human tumor cell lines using a microculture tetrazolium assay *Cancer Res.*, 48:589–601, 1988; Carmichael, J., DeGraff, W. G., Gazdar, A. F., Minna, J. D. and Mitchell, J. B., Evaluation of a tetrazolium-based semiautomated colorimetric assay: Assessment of chemosensitivity testing. *Cancer Res.*, 47:936–942, 1987; McHale, A. P., McHale, L., Use of a tetrazolium based colorimetric assay in assessing photoradiation therapy in vitro. *Cancer Lett.*, 41:315–321, 1988; and Saxton, R. E., Huang, M. Z., Plante D., Fetterman, H. F., Lufkin, R. B., Soudant, J., Castro, D. J., Laser and daunomycin chemophototherapy of human carcinoma cells. *J. Clin. Laser Med. and Surg.*, 10(5):331–336, 1992.)

Analysis of absorption readings at 550 nm were analyzed by grouping wells of the same test conditions and verifying differences occurring between control and the various peptide concentration treatments by one-way ANOVA. Once statistical significance was achieved, P <0.05, each test group was compared to its paired control group by Student's T-test within each 96 well plate. A statistical significance was considered when P <0.05 was achieved.

The results of the MTT viability assays for PANC-1 and MiaPaCa-2 36 hours after exposure to either PYY or BIM-43004-1 are shown in the following Table. Percent reduction in cell growth is described as compared to control cell growth with normal saline inoculation.

TABLE I

| | Percent Reduction in Tumor Growth(%) Compound Compared to Control | | |
|---|---|---|---|
| PEPTIDE | CONCENTRATION | PANC-1 | Mia PaCa-2 |
| PYY | 250 pmol | 25.7% | 15.4% |
| PYY | 25 pmol | 14.7% | 12.8% |
| PYY | 2.5 pmol | 9.8% | 0.5% |
| Analog #1 | 400 pmol | 18.2% | 37.1% |
| Analog #1 | 40 pmol | 21.3% | 33.6% |
| Analog #1 | 4 pmol | 10.5% | 28.3% |
| | *P < 0.05 by ANOVA | | |

As shown in the above Table, the MTT assay confirmed a significant decrease in the cell growth of both pancreatic tumor cell lines when PYY and Analog #1 were added to the cells.

EXAMPLE 2

Demonstration of Anti-Proliferative Activity In Vivo

In this example, the effectiveness of PYY and Analog #1 in reducing proliferation of a pancreatic ductal adenocarcinoma in vivo is demonstrated.

The human pancreatic ductal adenocarcinoma Mia Paca-2 was examined for in vivo growth inhibition by peptide YY and Analog #1. Seventy thousand to 100,000 human Mia PaCa-2 cells were orthotopically transplanted into 48 male athymic mice. After one week, the animals were treated with either PYY or Analog #1 at 200 pmol/kg/hr via mini-osmotic pumps for four weeks. The paired cultures received saline. At sacrifice, both tumor size and mass were measured.

Control mice had significant human cancer growth within the pancreas as evidenced by histologic sections. At 9 weeks, ninety percent (90%) of control mice had substantial metastatic disease. Tumor mass was decreased by 60.5 % in Analog #1 treated mice and 27% in PYY treated mice.

EXAMPLE 3

Intravenous Treatment of Benign Pancreatic Tumor In Vivo

A patient having a pancreatic serous cyst adenoma is treated as follows in accordance with the present invention:

A sterile saline or distilled water solution containing from 7200 pmol to 864,000 pmol PYY or Analog gl in 1000 cc of total volume is administered intravenously to the patient at a rate of 12 to 24 ml/hour. The solution is administered so as to provide a delivery rate of PYY or Analog #1 on the order of about 200 pmol/kg/hour to about 400 pmol/kg/hour. The intravenous administration is conducted for 6 to 36 hours at a time depending upon patient tolerance. Standard intravenous delivery equipment is utilized. The treatment is repeated as required to achieve reduction in tumor cell proliferation.

EXAMPLE 4

Perfusion Treatment of Benign Pancreatic Tumor In Vivo

A patient having a pancreatic solid-cystic tumor is treated as follows in accordance with the present invention:

A sterile saline or distilled water solution containing from PYY or Analog #1 is administered by directly perfusing the solution into the tumor site. The concentration of PYY or Analog #1 in the solution and the delivery rate are chosen to provide delivery of 200 pmol/kg/hour to 400 pmol/kg/hour. Perfusion is accomplished using Alzet Mini-Osmotic pumps implanted subcutaneously which are connected to a polyethylene catheter tunneled through the abdominal musculature.

EXAMPLE 5

Implantation Treatment of Malignant Pancreatic Tumor In Vivo

A patient having a carcinoma arising from a pancreatic duct is treated as follows in accordance with the present invention:

An implant device is prepared which is capable of delivering from 100 pmol to 1000 pmol of PYY or Analog #1 directly to the tumor for periods of up to 2 weeks. The device is implanted adjacent to the tumor in accordance with standard implant insertion procedures.

EXAMPLE 6

Intravenous Treatment of Malignant Pancreatic Tumor In Vivo

A patient having a carcinoma arising from a pancreatic islet is treated as follows in accordance with the present invention:

A sterile saline solution containing PYY or Analog #1 is administered intravenously to the patient via a peripheral venous catheter or central venous catheter. The delivery rate is selected so as to provide a dosage of from about 200 pmol/kg/hour to about 400 pmol/kg/hour of either PYY or Analog #1.

EXAMPLE 7

Perfusion Treatment of Malignant Pancreatic Tumor In Vivo

A patient having a carcinoma arising from a pancreatic acini is treated as follows in accordance with the present invention:

A sterile saline solution containing PYY or Analog #1 is administered by directly perfusing the solution into the tumor site. The same perfusion procedure used in Example 4 is followed. The concentration of PYY or Analog #1 and perfusion rate are selected to provide delivery of 200 pmol/kg/hour to 404 pmol/kg/hour of either peptide YY or Analog #1.

The publications and other reference materials referred to herein to describe the background of the invention and to provide additional details regarding its practice are all hereby incorporated by reference.

The foregoing description has been limited to specific embodiments of this invention. It will be apparent, however, that variations and modifications may be made to the invention, with the attainment of some or all of the advantages of the invention. Such embodiments are also within the scope of the following claims.

---

What is claimed is:

1. A method of inhibiting proliferation of pancreatic tumors in mammals, said method comprising the step of administering to said mammal an effective amount of PYY or a PYY agonist.

2. A method of claim 1, wherein said pancreatic tumor is benign.

3. A method of claim 1, wherein said pancreatic tumor is malignant.

4. The method of claim 1, wherein said administering is effected parenterally.

5. The method of claim 4, wherein said administering is effected intravenously.

6. The method of claim 4, wherein said administering is effected subcutaneously.

7. The method of claim 4, wherein said administering is effected by implantation.

8. The method of claim 4, wherein said administering is effected by perfusion.

9. The method of claim 2, wherein said administering is effected parenterally.

10. The method of claim 9, wherein said administering effected intravenously.

11. The method of claim 9, wherein said administering is effected subcutaneously.

12. The method of claim 9, wherein said administering is effected by implantation.

13. The method of claim 9, wherein said administering is effected by perfusion.

14. The method of claim 3, wherein said administering is effected parenterally.

15. The method of claim 14, wherein said administering is effected intravenously.

16. The method of claim 14, wherein said administering is effected subcutaneously.

17. The method of claim 14, wherein said administering is effected by implantation.

18. The method of claim 14, wherein said administering is effected by perfusion.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 36 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: porcine peptide YY ( x i ) SEQUENCE DESCRIPTION: SEQ ID NO:1:

```
Tyr Pro Ala Lys Pro Glu Ala Pro Gly Glu Asp Ala Ser Pro Glu Glu
 1               5                  10                  15
Leu Ser Arg Tyr Tyr Ala Ser Leu Arg His Tyr Leu Asn Leu Val Thr
            20                  25                  30
Arg Gln Arg Tyr
            35
```

( 2 ) INFORMATION FOR SEQ ID NO:2:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: HUMAN PEPTIDE YY ( x i ) SEQUENCE DESCRIPTION: SEQ ID NO:2:

```
Tyr Pro Ile Lys Pro Glu Ala Pro Gly Glu Asp Ala Ser Pro Glu Glu
 1               5                  10                  15
Leu Asn Arg Tyr Tyr Ala Ser Leu Arg His Tyr Leu Asn Leu Val Thr
            20                  25                  30
Arg Gln Arg Tyr
            35
```

( 2 ) INFORMATION FOR SEQ ID NO:3:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: HUMAN NEUROPEPTIDE Y ( x i ) SEQUENCE DESCRIPTION: SEQ ID NO:3:

```
Tyr Pro Ser Lys Pro Asp Asn Pro Gly Glu Asp Ala Pro Ala Glu Asp
 1               5                  10                  15
Met Ala Arg Tyr Tyr Ser Ala Leu Arg His Tyr Ile Asn Leu Ile Thr
            20                  25                  30
Arg Gln Arg Tyr
            35
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide (v i) ORIGINAL SOURCE:
    (A) ORGANISM: PORCINE NEURAL PEPTIDE Y (x i) SEQUENCE DESCRIPTION: SEQ ID NO:4:

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (v i) ORIGINAL SOURCE:
        (A) ORGANISM: peptide YY analog #1

(x i) SEQUENCE DESCRIPTION: SEQ ID NO:5:

Ala Ser Leu Arg His Trp Leu Asn Leu Val Thr Arg Gln Arg Tyr
1               5                   10                  15